United States Patent
Schmidt (10) Patent No.: US 8,934,692 B2
(45) Date of Patent: Jan. 13, 2015

(54) METHOD FOR DETERMINING A PET IMAGE DATA RECORD

(75) Inventor: Sebastian Schmidt, Weisendorf (DE)

(73) Assignee: Siemens Aktiengesellschaft, Munich (DE)

(*) Notice: Subject to any disclaimer, the term of this patent is extended or adjusted under 35 U.S.C. 154(b) by 123 days.

(21) Appl. No.: 13/415,934

(22) Filed: Mar. 9, 2012

(65) Prior Publication Data
US 2012/0230571 A1     Sep. 13, 2012

(30) Foreign Application Priority Data
Mar. 11, 2011  (DE) .................. 10 2011 005 435

(51) Int. Cl.
G06K 9/00 (2006.01)
A61B 6/03 (2006.01)
A61B 5/055 (2006.01)
A61B 6/00 (2006.01)
A61B 5/00 (2006.01)

(52) U.S. Cl.
CPC .............. A61B 6/037 (2013.01); A61B 5/055 (2013.01); A61B 6/5258 (2013.01); A61B 6/54 (2013.01); A61B 6/4417 (2013.01); A61B 5/0033 (2013.01)
USPC .......................... 382/131; 382/128; 600/411

(58) Field of Classification Search
None
See application file for complete search history.

(56) References Cited

U.S. PATENT DOCUMENTS

| | | | |
|---|---|---|---|
| 7,327,138 B2 | 2/2008 | Krieg et al. | |
| 7,719,277 B2 | 5/2010 | Eberler et al. | |
| 7,859,261 B2 | 12/2010 | Jattke et al. | |
| 7,923,691 B2 | 4/2011 | Ladebeck | |
| 8,108,026 B2* | 1/2012 | Eberler et al. | 600/411 |
| 8,290,568 B2* | 10/2012 | Pichler et al. | 600/411 |
| 8,600,482 B2* | 12/2013 | Schmidt | 600/436 |
| 8,768,432 B2* | 7/2014 | Ladebeck | 600/411 |
| 2005/0096537 A1* | 5/2005 | Parel et al. | 600/427 |
| 2006/0058641 A1 | 3/2006 | Krieg et al. | |
| 2006/0072799 A1* | 4/2006 | McLain | 382/128 |
| 2008/0135769 A1 | 6/2008 | Rosen | |

(Continued)

FOREIGN PATENT DOCUMENTS

DE    102004043889 A1    3/2006
DE    102006037047 A1    2/2008
(Continued)

OTHER PUBLICATIONS

Albrecht et al.: "Gadolinium-DTPA as X-ray contrast medium in clinical studies", The British Journal of Radiology, 73 (Aug. 2000) p. 878-882.

(Continued)

*Primary Examiner* — Nancy Bitar
(74) *Attorney, Agent, or Firm* — Harness, Dickey & Pierce, P.L.C.

(57) ABSTRACT

A method is disclosed for determining a PET image data record of a target area from PET image data recorded during a period using a combined PET device provided with an additional imaging modality, an attenuation map describing the absorption of photons in the imaging area being used for attenuation correction of the PET image data. In at least one embodiment of the method, as a function of at least one change in the attenuation in the imaging area during the period, the PET image data are divided into at least two PET image data groups of different time domains of the period and are evaluated differently with respect to consideration of the attenuation.

18 Claims, 2 Drawing Sheets

(56) References Cited

U.S. PATENT DOCUMENTS

| | | |
|---|---|---|
| 2008/0317194 A1* | 12/2008 | Gagnon et al. ............... 378/4 |
| 2009/0105583 A1 | 4/2009 | Martin et al. |
| 2009/0110256 A1* | 4/2009 | Thielemans et al. .......... 382/131 |
| 2009/0206263 A1* | 8/2009 | Rahman ................... 250/341.1 |
| 2010/0268063 A1* | 10/2010 | Schmidt ..................... 600/411 |
| 2011/0123083 A1* | 5/2011 | Ojha et al. .................. 382/131 |
| 2011/0251480 A1* | 10/2011 | Graves et al. ............... 600/411 |
| 2012/0095322 A1* | 4/2012 | Tsekos et al. ............... 600/411 |

FOREIGN PATENT DOCUMENTS

| | | |
|---|---|---|
| DE | 102007013564 A1 | 9/2008 |
| DE | 102007044860 A1 | 12/2008 |
| DE | 102007044874 A1 | 4/2009 |
| DE | 102008022816 A1 | 11/2009 |
| DE | 102009017439 A1 | 10/2010 |

OTHER PUBLICATIONS

German Office Action for German Patent Application No. DE 10 2011 005 435.9 (Not Yet Published).

German Priority document for German Patent Application No. DE 10 2011 005 435.9 (Not Yet Published).

* cited by examiner

METHOD FOR DETERMINING A PET IMAGE DATA RECORD

PRIORITY STATEMENT

The present application hereby claims priority under 35 U.S.C. §119 to German patent application number DE 10 2011 005 435.9 filed Mar. 11, 2011, the entire contents of which are hereby incorporated herein by reference.

FIELD

At least one embodiment of the invention generally relates to a method for determining a PET image data record of a target area from PET image data recorded during a period using a combined PET device provided with an additional imaging modality, an attenuation map describing the absorption of photons in the imaging area being used for attenuation correction of the PET image data.

BACKGROUND

Positron emission tomography (PET) is an imaging method which is mainly used in medical imaging. In the process images of living organisms are produced in which the distribution of a previously administered weakly radioactively marked substance is made visible in the organism, the substance having been enriched in the organism such that biochemical and physiological processes can be imaged. The substances are called radiopharmaceutical agents, with radionuclides, which emit positrons on decomposition, being suitable in particular. After a short distance, by way of example 2-3 mm, the positrons interact with an electron and what is referred to as annihilation occurs. In the process both particles, positron and electron, are destroyed and two high-energy photons are produced with energy of 511 keV each. These photons distance themselves from each other at an angle of about 180° and can be measured, by way of example, on a detector ring where they simultaneously meet at two points. Evidence of positron emission and an estimation of the location of annihilation is possible due to the coincidence of the two measuring results.

However, it should be noted in this connection that the photons emitted by the radiopharmaceutical agent are partially absorbed by the tissue surrounding them or other substances in the imaging region. This attenuation must be taken into consideration in the image reconstruction since image artifacts that are disruptive in other respects are produced. It is known in this regard to determine a data record of attenuation values in the target area, frequently called an attenuation map or μ-map. The attenuation map contains the specific absorption for each image voxel and is used for correction.

PET is often used together with other imaging modalities which may then also be used to determine the attenuation map. Thus, by way of example in the case of combined PET computerized tomography (CT) systems this data record is produced from a CT data record which is measured before the PET examination. The attenuation in the case of computerized tomography (about 120-140 kV tube voltage) is converted into the PET attenuation (511 keV), it being possible to optionally employ additional transformation steps, by way of example smoothing filters, segmenting and the like, as is known from the prior art.

Recently, however, PET has been combined with magnetic resonance (MR) in which the examined object is positioned in an MRI device in a comparatively static homogeneous basic magnetic field, so the nuclear spin thereof. is oriented along the basic magnetic field. High-frequency excitation pulses are beamed into the examined object to activate nuclear spin resonances, the activated nuclear spin resonances are measured and MR images reconstructed on the basis thereof. Fast-switched magnetic gradient fields are superimposed on the basic magnetic field for the purpose of site coding. Magnetic resonance allows excellent depiction in particular of soft tissues with selectable contrasts.

To be able to use the advantages of PET and magnetic resonance in combination, combined PET-MR devices have been proposed, wherein, however, there is the problem of determination of the attenuation map being more difficult in this case since there is initially no correlation between the MR signal strength and PET attenuation. Various methods are known, however, in order to still be able to derive an attenuation map from a magnetic resonance data record, the magnetic resonance data record being registered, by way of example, on an atlas describing the target area and in which corresponding attenuation values are allocated to various anatomical structures to thus obtain an attenuation map with which the PET image data records may subsequently be corrected. A procedure of this kind is known, by way of example, from DE 10 2004 043 889 A1. The use of movement corrections on the attenuation map has also been proposed in this connection, as is described, by way of example, by US 2008/0135769.

One problem with this procedure, however, is that, even during acquisition, the PET data changes forming the basis of the PET image data record can occur in the target area or even in the entire imaging area. Such changes can be caused, by way of example, by patient movements. Another significant interference factor, however, is the injection of contrast medium, by way of example magnetic resonance contrast medium, during the PET examination.

Such magnetic resonance contrast medium may, by way of example, be gadolinium chelates. Gadolinium (atomic number 64) significantly reduces X-rays and gamma rays and is also used as an X-ray contrast medium, cf. by way of example the article in The British Journal of Radiology, 73 (2000), 878-882 in this regard. The resulting gadolinium concentration is so low in large parts of an examined body that it may be ignored. Regions in which the contrast medium flows from the vein in concentrated form are a problem, however—in the case of injection into the arm veins typically the arm veins, the Vena brachiocephalica, the upper Vena cava and the heart. Furthermore, retrograde flow into the Vena jugularis may occur. This can lead to artifacts in the PET reconstruction of the adjoining areas (upper arm, throat, apex of the lung, heart, etc.).

The problem basically occurs with respect to the second imaging modality whenever a contrast medium is administered during the recording of PET data. This is less often the case with combined CT-PET devices since there the CT scans are usually carried out before the PET examinations. The problem of the other changes in the imaging area basically affects all devices in which PET is combined with an additional imaging modality.

SUMMARY

At least one embodiment of the invention is directed to a method for determining PET image data records in which artifacts, which result due to a change in the imaging area during PET data recording, may be reduced or even avoided altogether.

At least one embodiment of the invention is directed a method that, as a function of at least one change in the attenuation in the imaging area during the period, the PET image data are divided into at least two PET image data groups of different time domains of the period and are evaluated differently with respect to consideration of the attenuation.

According to at least one embodiment of the invention the PET measuring time, the period, is therefore divided into time domains, which can also be called 'time slices' by way of example. It should be noted at this point already that a time domain can also include a plurality of separate time intervals or time periods, by way of example if a change occurs several times in the same way, although it is also conceivable for a time domain to be just a single, defined time interval.

More specifically, it is therefore being proposed that an imaging time, which lies within the period, is allocated to each recorded PET image datum. It is therefore possible to allocate a PET image datum to the time domains and therefore the groups. A separate attenuation map, or, more generally, attenuation correction, can then be allocated to each of the time domains, wherein the changes are taken into consideration. One PET data record respectively can in particular be reconstructed for the individual time domains, the PET data records finally being combined to form the PET image data record. It should be mentioned at this point already that consideration of attenuation can also mean that the PET image data of a certain time domain are completely discarded, a fact which will be discussed in more detail below.

At least one embodiment of the inventive method therefore makes it possible to take into consideration changes in the target area, or in the remaining imaging area, which occur during the period of the PET data recording in that the PET image data can be sorted as a function of time and therefore as a function of change, by way of example with respect to the administration of a contrast medium or an observed movement. Different attenuation correction of the PET image data groups occurs thereafter as a function of the respective change. Artifacts, which are based on changes during PET data recording, can thus be reduced and in particular even completely avoided, so higher quality PET image data records can be obtained.

At least one embodiment of the inventive method is primarily based on combined magnetic resonance-PET devices but use of the method is obviously also conceivable for other combined devices.

In a development of at least one embodiment of the invention it may be provided that during a time domain of the change, which is shorter than the remaining period, and/or during a change in the attenuation maps which exceeds at least one threshold compared with at least one other time domain, the PET image data of the time domain of the change are not taken into consideration when determining the image data record. As has already been described, it is therefore conceivable to ignore insignificant parts of the PET data or data whose correction would be too laborious or impossible. If, by way of example, a magnetic resonance contrast medium is administered to a patient to be examined, the data from the instant of administration to the instant at which the contrast medium has sufficiently dispersed in the body can be allocated to a group which is then discarded. Artifacts are thus avoided.

As already mentioned, it may be provided that one PET data record respectively is determined for at least two, in particular all, PET image data groups. It should be noted at this point that it is obviously also conceivable to use the PET data records, which are reconstructed for the individual image data groups, as separate PET image data records. By way of example, in the case where the change is a movement, a four-dimensional PET image data record can be produced therefore or certain movement states can be examined individually. It is particularly advantageous in the case of such a movement, however, if the PET data records are merged to form a common image data record. For this purpose it may be provided that at least two PET data records determined from PET image data groups corresponding to different movement states of the target area are merged by means of registering, in particular registering of the PET records, and/or secondary image data records recorded using the additional modality in the movement states, and/or by taking into consideration movement data describing the movement of the target area, to form a movement-compensated PET image data record.

As already mentioned, registering of the PET data records is possible in this connection but in some cases it is preferred when additional external data are at least considered. Secondary image data records recorded in the movement states using the additional modality are expedient here, by way of example magnetic resonance image data records therefore which show the anatomy very clearly and from which a change resulting from a movement can be easily determined. Registering methods of this kind are largely known and do not need to be illustrated in more detail here. However, it is also possible to use additional data, by way of example the data from diverse movement sensors, which can be implemented by way of example as a camera observing a patient or position sensors fixed to the patient. Obviously a wide range of possibilities is conceivable for reproducing a movement. Reference is made to the fact that a method of this kind can also be used for periodic, organ-related movements, by way of example respiration and/or heartbeat. Signals from an ECG device by way of example can be considered for determining the heartbeat. Respiration signals can also be received via a respiration belt. With a combined PET-magnetic resonance device it is also expedient to use what are known are navigators by way of example, i.e. one-dimensional MR measurements from which an organ movement can be easily derived.

It can expediently be provided that different attenuation maps are used for attenuation correction for at least two PET image data groups. In this case the different attenuation correction therefore manifests itself in the use of different attenuation maps, so it may by way of example be provided that two PET data records are reconstructed which are then attenuation-corrected using the different attenuation maps, so the two PET data records may then be combined without problems to form the PET image data record. Of course this is also conceivable for more than two PET image data groups, and in particular for all PET image data groups.

To determine the different attenuation maps it may particularly advantageously be provided that at least one secondary image data record of the additional imaging modality, is recorded, in particular in the respective time domain, for at least two PET image data groups, in particular all image data groups, the different attenuation maps being determined using the secondary image data record. The secondary image data record can particularly expediently again be a magnetic resonance image data record from which attenuation maps can then be derived in a known manner. In other words, secondary image data records are generated, ideally in the time domains themselves, from which a plurality of attenuation maps are calculated which can then be used for the PET image data groups allocated to the time domains. In the case of a contrast medium injection during the PET examination, by way of example one magnetic resonance secondary image data record can be recorded during the injection and one before. Two attenuation maps are then calculated from these data records which are used on the respective PET image data, which have been recorded before or after injection. It should be noted that the number of attenuation maps can also be smaller than the number of PET data records.

In a very specific embodiment of the inventive method it may therefore be provided that in the case of a change caused by the administration of contrast medium and when using magnetic resonance as the second modality, the influence of the contrast medium on the attenuation of the photons, in particular on the attenuation map, is determined with the aid of at least one magnetic resonance subtraction image. A magnetic resonance image can be recorded without contrast medium, in particular immediately before the administration of contrast medium, and at least one magnetic resonance image during the change due to the contrast medium, the at least one subtraction image being determined by subtraction of the magnetic resonance image without contrast medium from a magnetic resonance image with contrast medium. The idea behind the use of magnetic resonance subtraction images is mainly that a common method for determining attenuation maps from magnetic resonance images includes the anatomy being registered by way of example using an anatomical atlas, with attenuation maps than being allocated to the different anatomical structures in the anatomical atlas, so as soon as a pixel of the magnetic resonance image is allocated to an anatomical structure an attenuation value can also be allocated to this pixel. However, since contrast medium is not a conventional constituent of a body to be examined, although the attenuation of contrast medium is by all means known, information which shows where exactly contrast medium can be found is useful. Since the rest of the anatomy does not significantly change, ultimately the regions in which contrast medium is now present are obtained by subtraction of the magnetic resonance images, so an attenuation map can be determined. For this purpose it may be provided in a specific embodiment that an attenuation map is determined for the magnetic resonance image without contrast medium, wherein to determine the at least one attenuation map during the change due to administration of the contrast medium, additional attenuation values determined from the subtraction image are added to the attenuation values of the attenuation map without contrast medium. Since, in other words, by determining the subtraction image, which, moreover, can advantageously also be used in other applications, by way of example if it is a functional magnetic resonance examination anyway, it is known where contrast medium is in the body, and it is also known what the attenuation coefficients of the contrast medium are, the attenuation map can be supplemented simply by adding the contrast medium attenuation values to obtain the attenuation map with contrast medium.

In particular when considering periodic movements it is expedient if the duration of a time interval included in the time domain is shorter, in particular shorter by at least the factor 10, than a time of change, in particular a cycle duration, describing the time scale of the change, which occurs periodically in particular. In the case of a movement of the target area or the imaging area, for example the liver, which moves with the patient's breathing, the time intervals are selected such that their duration is much shorter than the frequency of the movement. In the case of rhythmical movements, such as the heartbeat or breathing, the PET image data can then be compiled in such a way that PET image data with substantially identical organ position are combined in one time domain. This means that it may be provided that in the case of a target area to be recorded and which periodically moves within the framework of the change, in particular a target area subject to the heartbeat and/or breathing, the time domains correspond to different phases of the movement. In one example when PET image data of an organ can be measured, by way of example, which organ moves with respiration, all data measured during inspiration can in the simplest case be compiled to form one PET image data group and all data measured during expiration can be compiled to form a second image data group. A separate attenuation map in particular then forms part of each PET image data group. In the case of the heart a more refined division can be made, so a time domain, and therefore a PET image data group, can be allocated to each phase of the cardiac cycle by way of example.

Determining the time domains can be at least partially pre-defined by an examination report. An examination report of this kind determines at which instant a magnetic resonance contrast medium is administered, so with the aid of these previously planned, in particular automated, procedures, it can be established from the outset which time domains are to be divided. When administering a contrast medium one time domain before the administration of contrast medium, one time domain in which the contrast medium spreads in the target area and one time domain after the contrast medium has dispersed can be defined by way of example, wherein, if the dispersed contrast medium has only a negligible influence on the PET image data, it may in this case be provided that the time domain without contrast medium is combined with the time domain with dispersed contrast medium to form a common time domain.

An examination report of this kind can also be used to define the imaging instants of secondary image data records to be recorded using the additional imaging modality in the examination report. Such secondary image data records can, as already mentioned, be used to determine attenuation maps for the PET image data groups of PET data records, or to take them into consideration. It is therefore conceivable by way of example if the injection of contrast medium is already firmly planned in the examination report, if corresponding images of the additional imaging modality, in particular MR images, are already planned, and in particular also take place automatically, so in any case secondary image data records can be obtained for the individual time domains.

In an advantageous development of at least one embodiment of the present invention it can, moreover, be provided that the time domains are determined at least partially with the aid of data describing the change. In such a case the individual time domains or the time intervals included therein are only fixed during the PET examination, so the PET image data can firstly be stored in what is known as 'list mode' and can then be divided into the PET image data groups. Specifically it may be provided that operating data of a contrast medium injector and/or a patient positioning device and/or measured data, in particular measured data from an ECG device and/or a respiration belt and/or measured data derived from a secondary image data record recorded using the additional imaging modality are taken into consideration as the data. If a combined PET-magnetic resonance device is used then the navigator measurements already mentioned are expedient for determining the magnetic resonance measured data, and these can be evaluated particularly advantageously with respect to the movement of organs. If it is necessary to move the patient into a different position during an examination by adjusting a patient positioning device, then the data thereof may also be taken into consideration to take account of movements and therefore changes in attenuation.

BRIEF DESCRIPTION OF THE DRAWINGS

Further advantages and details of the present invention emerge from the exemplary embodiments described below, and with reference to the drawings, in which.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
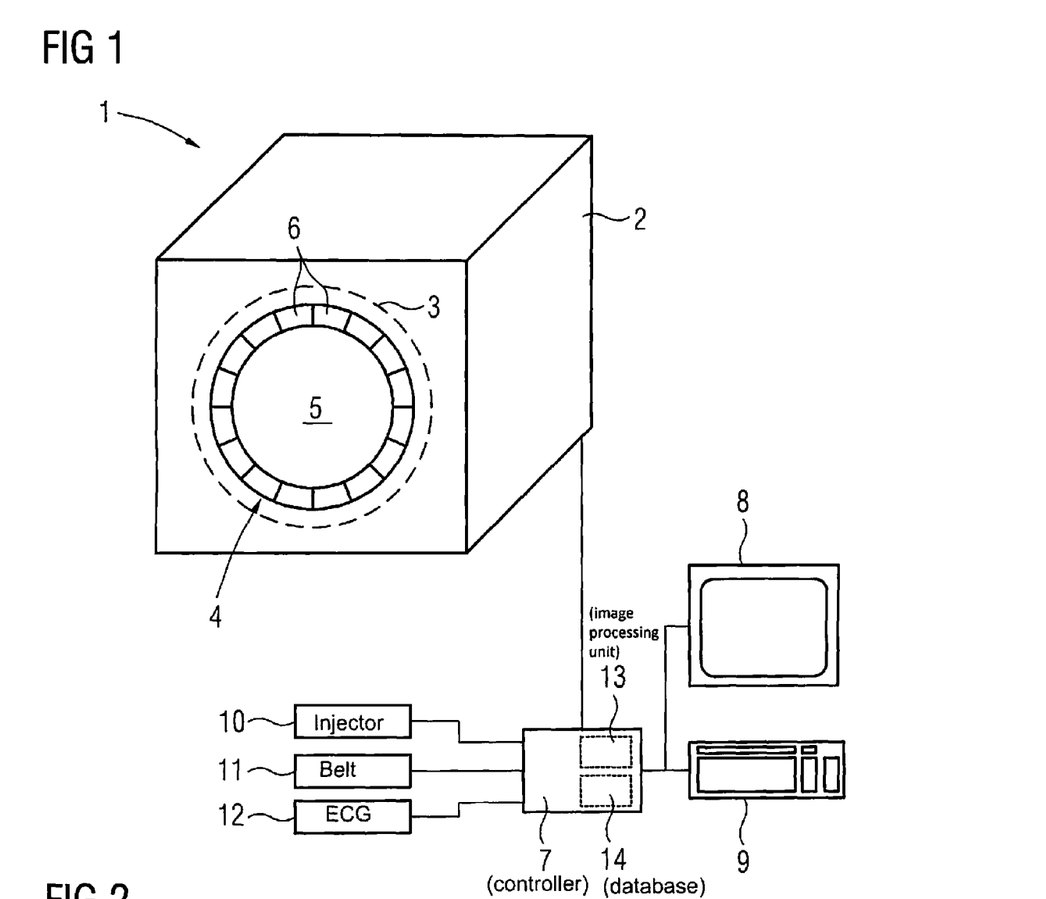
FIG. 1 shows a combined PET-magnetic resonance device.

FIG. 1 shows a schematic diagram of a combined PET-magnetic resonance device 1. The main magnet provided for the homogeneous main field for magnetic resonance imaging as an additional imaging modality is arranged in a magnet housing 2 which also encloses the gradient coils indicated at 3. A detection unit 4 is provided inside the gradient coils 3 and this defines the actual patient receiving device 5. In addition to PET detector blocks 6 the detection unit 4 comprises a high-frequency coil assembly whose longitudinal conductors (not shown in detail here) are guided in gaps between the detector blocks 6. An embodiment of this kind is described in more detail by way of example by DE 10 2006 037 047 A1. Obviously other assemblies are also conceivable which allow both magnetic resonance imaging as well as PET imaging.

Operation of the PET-MR device 1 is controlled by a controller 7 in which the inventive method can also be automatically carried out. A display device 8, by way of example a monitor, and an input device 9 are also provided. The controller 7 also receives data from a contrast medium injector 10, which it can also control, as well as from a respiration belt 11 and an ECG device 12 in the present example. Basically further devices with which the controller 7 communicates may of course also be provided.

In addition to an image processing unit 13 for reconstruction and processing of image data records, a database 14 is also provided in the controller 7 and contains an anatomical atlas with attenuation values allocated to the various anatomical structures, as well as attenuation data about MR contrast medium.

PET and MR images can therefore be actuated using the PET-MR device 1, and in particular also simultaneously. This means that while a PET examination, which often last several minutes and which can last 20 minutes by way of example, is being carried out, one or more magnetic resonance image data records can be recorded as secondary image data records. In the inventive method it is accordingly provided that secondary image data records and optionally additional data, by way of example that from devices 10-12, is used in order to divide PET image data recorded during a PET examination of a certain period into PET image data groups, which are allocated to certain different states of the object to be recorded, by way of example a patient, based on the attenuation, and which are treated differently in relation to attenuation within the framework of reconstruction of at least one PET image data record. This means a different attenuation correction is made. Such a change in the target area to be recorded (or in the entire recording area, here the patient receiving device 5) can be caused by movements by way of example. However, it is also conceivable for a change in the attenuation properties in the target area to be triggered by the administration of a contrast medium, here a magnetic resonance contrast medium.

Two examples for carrying out an embodiment of the inventive method shall therefore be described in more detail below.

Figure 2:
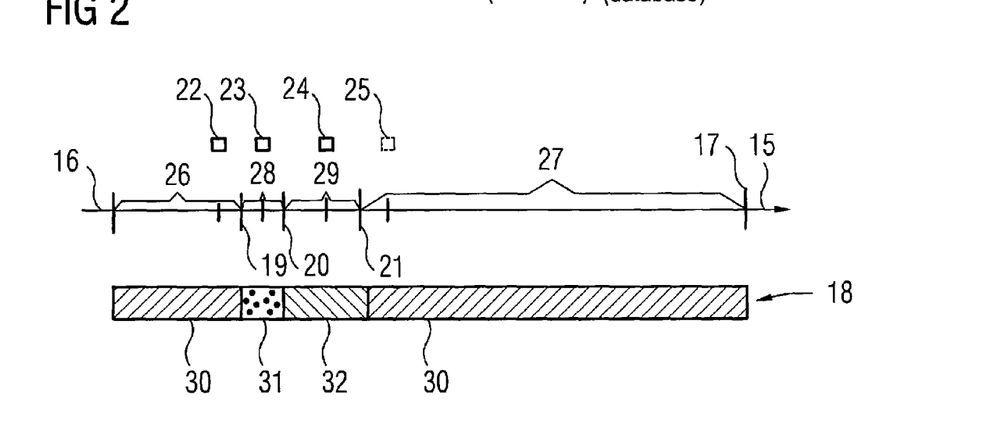
FIG. 2 shows a sketch of the time lapse during a PET examination.

In this regard FIG. 2 schematically shows in the form of a timeline 15 the course of a PET examination which begins at instant 16 and ends at an instant 17, by way of example twenty minutes later. The time between the instants 16 and 17 is therefore the period in which PET image data, which are symbolically illustrated at 18, are recorded. In the present case, by way of example after five minutes, at an instant 19 a magnetic resonance contrast medium is administered by the contrast medium injector 10. This contrast medium now spreads in the body of a patient to be imaged, wherein initially there are still highly localized concentrations up to an instant 20, by way of example 30 seconds or one minute after administration of the contrast medium, the contrast medium then continuing to disperse up to an instant 21 and finally being dispersed to such an extent (after instant 21) that only a negligible impairment of the PET recording mode occurs.

Instants 16, 17, 19, 20 and 21 are defined in an examination report, with the aid of which the controller 7 controls the components of the PET-MR device. Recording instants for magnetic resonance image data records are also already fixed in the examination report, a magnetic resonance image 22, which is recorded before the administration of contrast medium, a magnetic resonance image 23, which is taken directly after the administration of contrast medium before instant 20, and a magnetic resonance image 24, which is taken between instants 20 and 21, being shown by way of example in FIG. 2. Of course other magnetic resonance images may also be recorded as secondary image data records. An optional magnetic resonance image 25 after instant 21 is also illustrated purely by way of example. It should be noted at this point that the magnetic resonance images 22-24, optionally 25, can also be used for diagnostic purposes by way of example, in addition to the use in an embodiment of the inventive method.

The examination protocol, in which the instants 16, 19, 20, 21 and 17 are fixed, also fixes time domains in the case of stationary patients which represent a different attenuation in the patient. A first time domain is defined by the intervals 26 and 27. The contrast medium has hardly any influence in these intervals 26, 27. Intervals 26, 27, which, moreover, can also be considered as time slices, are therefore combined to form one time domain, the interval 28 between instants 19 and 20 and the interval 29 between instants 20 and 21 define further time domains which in this case include only one interval 28, 29.

Once the PET image data 18 has been stored with its recording instant it is accordingly possible to divide them into PET image data groups 30, 31 and 32 with the aid of the defined time domains.

The idea is accordingly to determine an attenuation map for all of these PET image data groups in order to determine a PET data record firstly for each of the PET image data groups 30-32 with the aid of these attenuation maps, it being possible to then combine the individual PET data records into a common PET image data record once they have all been correctly attenuation-corrected in accordance with the change that takes place in the patient due to the contrast medium.

Figure 3:
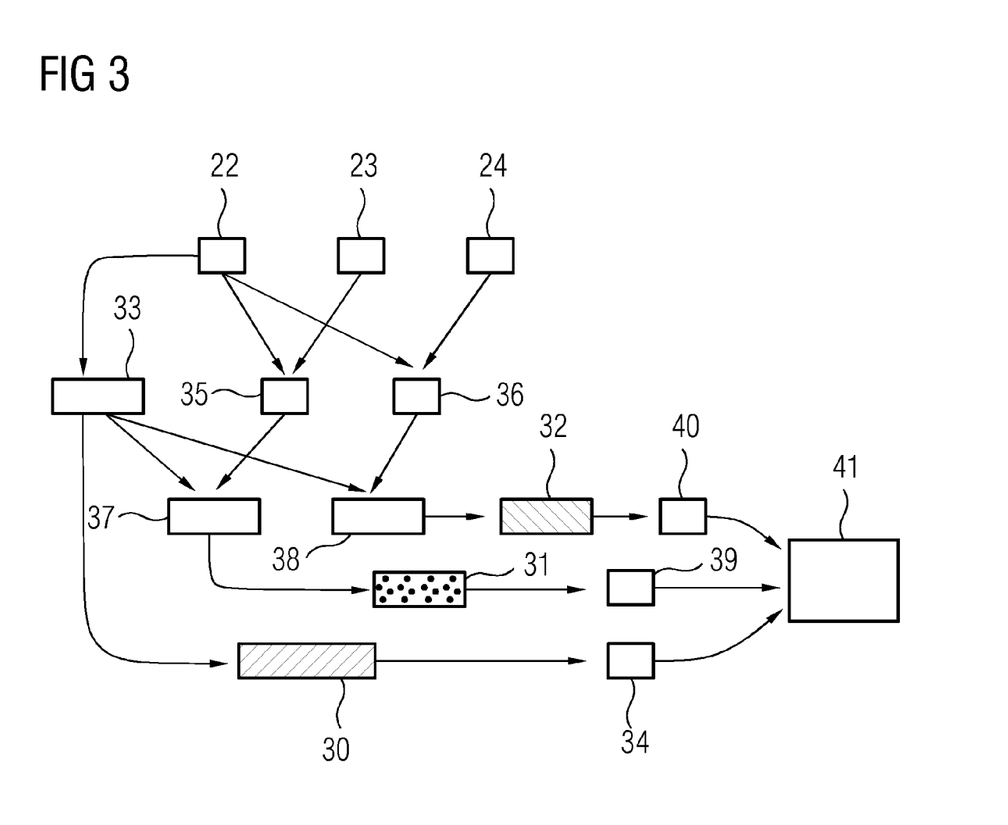
FIG. 3 shows a flowchart for part of an embodiment of the inventive method.

This procedure is described in more detail by FIG. 3. It should firstly be noted in this connection that the possibilities known from the prior art for determining attenuation maps are not suitable for taking the effect of contrast medium into consideration. As a rule it is usual for the magnetic resonance data to be segmented and to be allocated attenuation values by way of a reference data record or an anatomical atlas. There is no anatomical atlas of this kind contained in the database 14 of the controller 7. These anatomical atlases obviously do not contain information about where contrast medium might be present, however, and which attenuation value could be allocated to this contrast medium. Even if a reference data record with contrast medium is recorded, such a method can fail if, by way of example when creating the reference data record, the contrast medium was injected into the left arm vein and into the right during recording.

This problem is solved as follows within the scope of an embodiment of the inventive method. Firstly an attenuation map 33 is determined from the magnetic resonance image 22 with the known methods by way of anatomical atlases. These attenuation maps 33, which refer to the state without contrast medium, can then also subsequently be used directly to reconstruct an attenuation-corrected PET data record 34 from the PET image data of the PET image data group 30.

In order to also discover the attenuation due to the contrast medium in the intervals 28 and 29, the magnetic resonance image 22 is in each case deducted from the magnetic resonance images 23 and 24, so magnetic resonance subtraction images 35 and 36 are obtained which show where contrast medium is located and with the aid of the intensity also how high the contrast medium concentration is there. Attenuation values can accordingly in turn be allocated to the pixels in the subtraction images 35, 36 with the aid of the information about the attenuation values of the contrast medium stored in database 14, these attenuation values then being added in a following step to the attenuation values of the attenuation map 33 to obtain attenuation maps 37 and 38. Attenuation map 37 is then used to determine an attenuation-corrected PET data record 39 from the PET image data of PET image data group 31, while attenuation map 38 is used to obtain an attenuation-corrected PET data record 40 from the PET image data of PET image data group 32. Once PET data records 34, 39 and 40 have therefore all been correctly attenuation-corrected and there is no movement of the patient during the PET examination, the PET data records 34, 39 and 40 can now be compiled without problems into a lower-artifact, in particular artifact-free, PET image data record 41.

Figure 4:
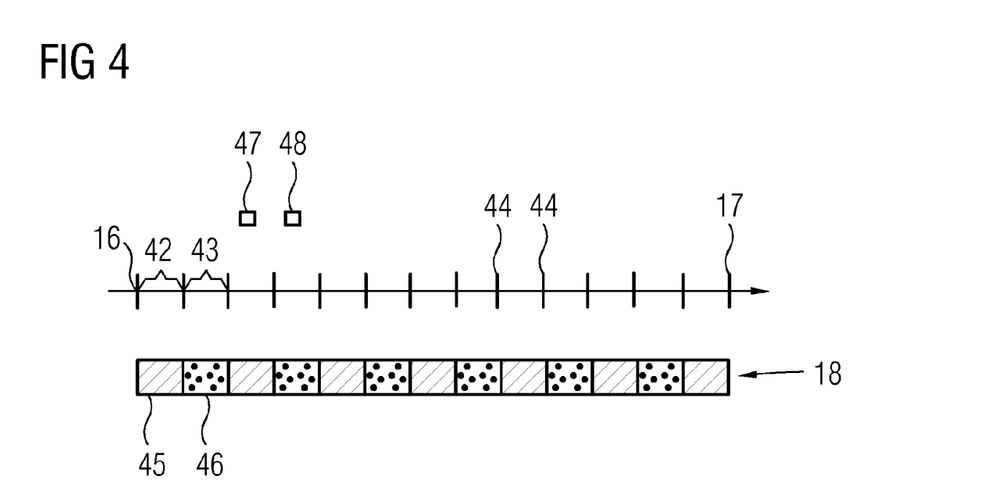
FIG. 4 shows a second sketch of the course of a PET examination.

FIG. 4 shows a further example, the change in the attenuation characteristic of the patient to be recorded being considered here on the basis of his regular breathing. PET image data recoding again begins at instant 16 and ends at instant 17. Since the target area is the liver moved by the patient's breathing, the respiration belt 11 accordingly measures whether an inspiration state or an expiration state currently exists. The change between the inspiration intervals 42 and the expiration intervals 43 is illustrated by the instants 44 indicated in FIG. 4.

In the case described in FIG. 4 the PET image data 18 are firstly recorded in a 'list mode' since allocation to PET image data groups firstly occurs dynamically due to measurement by way of the respiration belt 11. The PET image data 18 are then allocated to an inspiration PET image data group 45 and an expiration PET image data group 46 on the basis of the known instants 44.

During the PET examination it is, moreover, ensured that at least one magnetic resonance image 47, 48 is recorded during inspiration and during expiration. In the present case these are used not only to determine the attenuation maps, as already described with reference to FIG. 3, but elastic registering is also performed between the magnetic resonance images 47, 48 as secondary image data records which is subsequently used to likewise also register with each other the PET data records not yet registered, these records being obtained from PET image data groups 45, 46, and in turn to be able to combine them to form a PET image data record.

Of course an embodiment of the inventive method may also be applied to other movements, by way of example a movement caused by the heartbeat or other movements of the patient during the PET examination, which can also be recorded by way of example by other sensors. Although only two breathing times have been considered here for the purpose of simpler illustration, it is basically preferred if in the case of periodic movements intervals are considered which are much shorter than one period. In particular a separate PET image data group can be allocated to each cardiac phase of a cardiac cycle in the case of a heartbeat, so with sufficient data, a four-dimensional PET image data record may optionally even be produced. Accordingly a finer division may also be made with respect to the contrast medium in the exemplary embodiment according to FIGS. 2 and 3. Finally it should also be noted that combined contrast medium-induced and movement-induced changes in the target area to be recorded may of course also be dealt with together.

In a less preferred embodiment it may also be provided that, by way of example if the changes in attenuation are too great and/or only very sort intervals are involved, which are negligible compared with the overall PET data recording, [can be provided that] PET image data of a PET image data group are completely removed from evaluation, by way of example if a meaningful attenuation correction no longer seems possible.

LIST OF REFERENCE NUMERALS

1 PET-magnetic resonance device
2 magnet housing
3 gradient coil
4 detection unit
5 patient receiving device
6 PET detector block
7 controller
8 display device
9 input device
10 contrast medium injector
11 respiration belt
12 ECG device
13 image processing unit
14 database
15 timeline
16 instant
17 instant
18 PET image data
19 instant
20 instant
21 instant
22 magnetic resonance image
23 magnetic resonance image
24 magnetic resonance image
25 magnetic resonance image
26 interval
27 interval
28 interval
29 interval
30 PET image data group
31 PET image data group
32 PET image data group
33 attenuation map
34 PET data record
35 magnetic resonance subtraction image
36 magnetic resonance subtraction image
37 attenuation map
38 attenuation map
39 PET data record
40 PET data record
41 PET image data record
42 inspiration interval
43 expiration interval
44 instant
45 inspiration PET image data group
46 expiration PET image data group
47 magnetic resonance image
48 magnetic resonance image

What is claimed is:

1. A method for determining a PET image data record of a target area from PET image data recorded during a period using a combined PET device provided with an additional imaging modality, at least one attenuation map describing absorption of photons in the imaging area being used for attenuation correction of the PET image data, the method comprising:
dividing the PET image data, as a function of at least one change in the attenuation in the imaging area during the period due to an administered contrast medium, into at least two PET image data groups of different time domains of the period, wherein different attenuation maps are used for attenuation correction for at least two PET image data groups and at least one secondary image data record of the additional imaging modality is recorded for the at least two PET image data groups, the different attenuation maps being determined using the secondary image data record; and
evaluating the at least two PET image data groups differently with respect to consideration of the attenuation, wherein when using magnetic resonance as the additional imaging modality, an influence of the contrast medium on the attenuation of the photons is determined with the aid of at least one magnetic resonance subtraction image.

2. The method as claimed in claim 1, wherein the PET image data of the time domain of the at least one change are not taken into consideration when determining the PET image data record at least one of
during a time domain of the at least one change, which is relatively shorter than the remaining period, and
during a change in the at least one attenuation map which exceeds at least one threshold compared with at least one other time domain.

3. The method as claimed in claim 1, further comprising:
determining one PET data record for the at least two PET image data groups.

4. The method as claimed in claim 3, wherein at least two PET data records determined from PET image data groups corresponding to different movement states of the target area are merged to form a movement-compensated PET image data record.

5. The method as claimed in claim 1, wherein a duration of a time interval included in at least one of the time domains is relatively shorter than a time of a periodic change.

6. The method as claimed in claim 5, wherein, in the case of a periodically moving target area to be recorded within the framework of the change, the time domains correspond to different phases of the movement.

7. The method as claimed in claim 1, wherein the time domains are at least partially defined by an examination report.

8. The method as claimed in claim 7, wherein the imaging instants are also defined in the examination report by secondary image data records to be recorded using the additional imaging modality.

9. The method as claimed in claim 1, wherein the time domains are at least partially determined with the aid of data describing the change.

10. The method as claimed in claim 9, wherein operating data are taken into consideration as the data, the operating data being operating data of at least one of
a contrast medium injector,
a patient positioning device,
measured data from an ECG device,
measured data from a respiration belt and
measured data derived from a secondary image data record recorded using the additional imaging modality.

11. A method for determining a PET image data record of a target area from PET image data recorded during a period using a combined PET device provided with an additional imaging modality, an attenuation map describing absorption of photons in the imaging area being used for attenuation correction of the PET image data, the method comprising:

dividing the PET image data, as a function of at least one change in the attenuation in the imaging area during the period, into at least two PET image data groups of different time domains of the period; and evaluating the at least two PET image data groups differently with respect to consideration of the attenuation, wherein in the case of a change caused by administration of contrast medium and when using magnetic resonance as the second modality, an influence of the contrast medium on the attenuation of the photons is determined with the aid of at least one magnetic resonance subtraction image, and a magnetic resonance image without contrast medium, and at least one magnetic resonance image are recorded during the change due to the contrast medium, the at least one subtraction image being determined by subtraction of the magnetic resonance image without contrast medium from a magnetic resonance image with contrast medium.

12. The method as claimed in claim 11, wherein an attenuation map is determined for the magnetic resonance image without contrast medium, wherein to determine the at least one attenuation map, additional attenuation values determined from the subtraction image during the change due to addition of contrast medium are added to the attenuation values of the attenuation map without contrast medium.

13. The method as claimed in claim 3, wherein the one PET data record is determined for all of the PET image data groups.

14. The method as claimed in claim 4, wherein the merging is done by way of at least one of:

registering of the at least two PET records, by taking into consideration secondary image data records recorded in the movement states using the additional imaging modality, and by taking into consideration movement data describing the movement of the target area.

15. The method as claimed in claim 1, wherein at least one secondary image data record of the additional imaging modality is recorded in a time domain for all image data groups.

16. The method as claimed in claim 5, wherein the duration of a time interval included in the time domain is shorter at least by the factor 10 than a cycle duration, describing the time scale of the change, which occurs periodically.

17. The method as claimed in claim 1, wherein, in the case of a change caused by administration of contrast medium and when using magnetic resonance as the second additional imaging modality, an influence of the contrast medium on the attenuation map is determined with the aid of at least one magnetic resonance subtraction image.

18. A method for determining a PET image data record of a target area from PET image data recorded during a period using a combined PET device provided with an additional imaging modality, an attenuation map describing absorption of photons in the imaging area being used for attenuation correction of the PET image data, the method comprising:

dividing the PET image data, as a function of at least one change in the attenuation in the imaging area during the period, into at least two PET image data groups of different time domains of the period; and evaluating the at least two PET image data groups differently with respect to consideration of the attenuation, wherein in the case of a change caused by administration of contrast medium and when using magnetic resonance as the second modality, an influence of the contrast medium on the attenuation of the photons is determined with the aid of at least one magnetic resonance subtraction image, and a magnetic resonance image without contrast medium, immediately before administration of the contrast medium, and at least one magnetic resonance image are recorded during the change due to the contrast medium, the at least one subtraction image being determined by subtraction of the magnetic resonance image without contrast medium from a magnetic resonance image with contrast medium.

* * * * *